US00PP32716P3

(12) United States Plant Patent
Randag

(10) Patent No.: US PP32,716 P3
(45) Date of Patent: Dec. 29, 2020

(54) CALLA LILY PLANT NAMED 'DUBAI NIGHTS'

(50) Latin Name: *Zantedeschia sprengeri*
Varietal Denomination: Dubai Nights

(71) Applicant: Dümmen Group B.V., De Lier (NL)

(72) Inventor: Cecilius Jan-Jochem Randag, CJ 'T Zand (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/602,414

(22) Filed: Sep. 30, 2019

(65) Prior Publication Data

US 2020/0113102 P1 Apr. 9, 2020

Related U.S. Application Data

(60) Provisional application No. 62/766,205, filed on Oct. 4, 2018.

(51) Int. Cl.
*A01H 5/02* (2018.01)
*A01H 6/10* (2018.01)

(52) U.S. Cl.
USPC ..... Plt./490
CPC ..... *A01H 6/10* (2018.05)

(58) Field of Classification Search
USPC ..... Plt./490
CPC ..... A01H 5/02
See application file for complete search history.

(56) References Cited

PUBLICATIONS https://www.pumpkinbeth.com/2017/05/chelsea-flower-show-plant-year-2017/; May 30, 2017; 6 pages.*

* cited by examiner

*Primary Examiner* — Kent L Bell
(74) *Attorney, Agent, or Firm* — The Webb Law Firm

(57) ABSTRACT

'Dubai Nights' is a new variety of calla lily plant having purple colored spathes that produces 9-13 inflorescences per 14-16 cm tuber. The flower stems are about 37-51 cm in height. The leaves are green with many whitish spots and have a leathery texture.

1 Drawing Sheet

Botanical classification: *Zantedeschia sprengeri*.
Varietal denomination: 'Dubai Nights'.

BACKGROUND OF THE NEW PLANT

The present invention comprises a new and distinct cultivar of calla lily, botanically known as *Zantedeschia sprengeri* and hereinafter referred to by the cultivar name 'Dubai Nights'.

'Dubai Nights' is a product of a planned breeding program, which had the objective of creating *Zantedeschia* hybrids for pot flower production in a wide range of colors with a large, classic flower shape. The breeding program began in 1989, and the new cultivar is a seedling selected from the crossing of *Zantedeschia sprengeri* variety 'Memories' (female parent, U.S. Plant Pat. No. 27,823) with *Zantedeschia sprengeri* seedling Z020011-437 (male parent, unpatented). 'Dubai Nights' was selected in 2011 by the inventor in 't Zand, The Netherlands as one flowering plant within the progeny of the stated cross.

The first act of asexual reproduction of 'Dubai Nights' by tissue culture was performed by the inventor in September of 2013 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants grown from 12 to 14 weeks in 14 cm pots in 't Zand, The Netherlands under greenhouse conditions, which approximate those generally used in horticultural practice. Color references are made to The 2001 R.H.S. Colour Chart of The Royal Horticultural Society of London, 4$^{th}$ Edition, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Dubai Nights' which, in combination, distinguish this calla lily as a new and distinct cultivar:

1. Purple colored spathes with a crème colored edge;
2. Lanceolate leaf shape;
3. Numerous leaf maculations present; and
4. High inflorescence production.

Table 1 provides a comparison of 'Dubai Nights' to its parents, as well as *Zantedeschia sprengeri* variety 'Picasso' (U.S. Plant Pat. No. 15,282).

TABLE 1

| Variety | Relationship | Trait differences | Description |
|---|---|---|---|
| 'Dubai Nights' | New variety | Spathe color | Upper surface is RHS N79A, with a second color of RHS 2D to 3D |
| | | Plant height | 37-51 cm |
| 'Memories' | Female parent | Spathe color | Varies between RHS N186A and N186B |
| | | Plant height | 12-40 cm |
| Z020011-437 | Male parent | Spathe color | RHS 187A |
| | | Plant height | 30-42 |
| 'Picasso' | Known variety | Spathe color | Base color is RHS 1D, with a second color between RHS 79A-79B |
| | | Plant height | 50-65 cm |

BRIEF DESCRIPTION OF THE DRAWING

The accompanying photographic drawing illustrates the new variety, with the colors being as nearly true as is possible with color illustrations of this type.

DESCRIPTION OF THE NEW PLANT

Type: Deciduous.

Size:

*Height of the leaf canopy above the soil.*—39-41 cm.

*Height of top of inflorescences above the soil.*—37-51 cm.

*Diameter.*—40-50 cm.

Form: Semi-spreading.

Number of inflorescences per tuber:

*Size* 14-16 cm in diameter: 9-13 inflorescences.

Branches:

*Number.*—Plentiful.

*Color.*—Green Group RHS 143B.

*Young shoot color.*—Purple Group RHS 79A.

Leaves:

*Size.*—Width: 5.5-10 cm, with the broadest part of the leaf blade slightly below the middle. Length: 20-24 cm.

*Number per plant.*—21-33.

*Leaf blade lobes.*—Absent.

*Shape.*—Lanceolate.

*Apex.*—Apiculate.

*Base.*—Rounded.

*Margin.*—Entire; having a color of Yellow-Green Group RHS N144B.

*Color.*—Upper surface: Green Group RHS 138B, with numerous White Group RHS 155B maculations present. Lower surface: Green Group RHS 137C, with White Group RHS 155D maculations present.

*Veins.*—Configuration: Pinnate. Color: Yellow-Green Group RHS 145B.

*Surface texture.*—Smooth (both surfaces).

*Petiole.*—Length: 21-27 cm. Diameter: Average of 20 mm. Color: The base is Red-Purple Group RHS 59B, the upper part is Green Group RHS 143B.

Roots:

*Color.*—White Group RHS 155C.

*Branching description.*—Fibrous root system. Several main roots emerge from the top of the tuber and form a small number of lateral roots.

Spathe:

*Size.*—Length (measured from opening to tip): 8-10 cm. Width: 4-7 cm. Height: 6-8 cm.

*Color.*—Throat spot: Absent. Upper surface: Purple Group RHS N79A, with a second color of Yellow Group RHS 2D to 3D. Lower surface: Purple Group RHS N77A.

*Vein color.*—Purple Group RHS N79A.

*Shape.*—Funnel.

*Apex.*—Acuminate.

*Base.*—Amplexicaul.

*Margin.*—Entire.

Spadix:

*Shape.*—Cylinder.

*Size.*—Length: 27-32 mm. Diameter: 10-15 mm.

*Color.*—From Yellow Group RHS 13A to Red-Purple Group RHS 71A.

*Position relative to spathe.*—Upright.

*Female flower.*—Number: 40-60. Shape: Pyramid. Height: 3 mm. Diameter: 4 mm.

*Male flower.*—Number: 120-180. Shape: Cone. Height: 2 mm. Diameter: 0.2 mm.

Peduncle:

*Size.*—Length: 31-41 cm. Diameter: 20-30 mm.

*Color.*—The upper part is Green Group RHS 143C, the lower part is Red-Purple Group RHS 60B.

*Texture.*—Smooth.

Reproductive organs:

*Location of female organs.*—Basal position of the spadix.

*Location of male organs.*—Upper position of the spadix.

*Perianth.*—Conspicuous.

*Stamens.*—Presence: Not visible before pollen release. Number: Between 480 and 600. Pollen amount: Abundant; similar to 'Picasso' (U.S. Plant Pat. No. 15,282). Color: Between White Group RHS 155B and 155C.

*Anther.*—Shape: Round. Length: Less than 1 mm. Color: Between Yellow Group RHS 8B and 8C.

*Filament.*—Length: Less than 1 mm. Color: White Group RHS 155D.

*Pistils.*—Number: 15 to 30. Length beyond perianth: About 1 mm.

*Stigma.*—Shape: Round. Size: Less than 1 mm.

*Style.*—Length: Less than 1 mm. Color: Between Yellow Group RHS 8B and 8C.

*Ovaries.*—Texture: Smooth. Length: Between 1 to 10 mm. Width: Between 1 to 10 mm. Color: The top color is Green-Yellow Group RHS 1C, the bottom color is Purple Group RHS N79A.

Disease resistance: No unusual susceptibility/resistance to diseases noticed to date.

Pest resistance: No unusual susceptibility/resistance to pests noticed to date.

Heat tolerance: No heat tolerance.

Hardiness: Not hardy.

Flowering: In general, the time from planting to first flowering takes eight weeks.

Lastingness: About two weeks on the plant.

Fragrance: None.

I claim:

1. A new and distinct variety of calla lily plant named 'Dubai Nights' as herein described and illustrated.

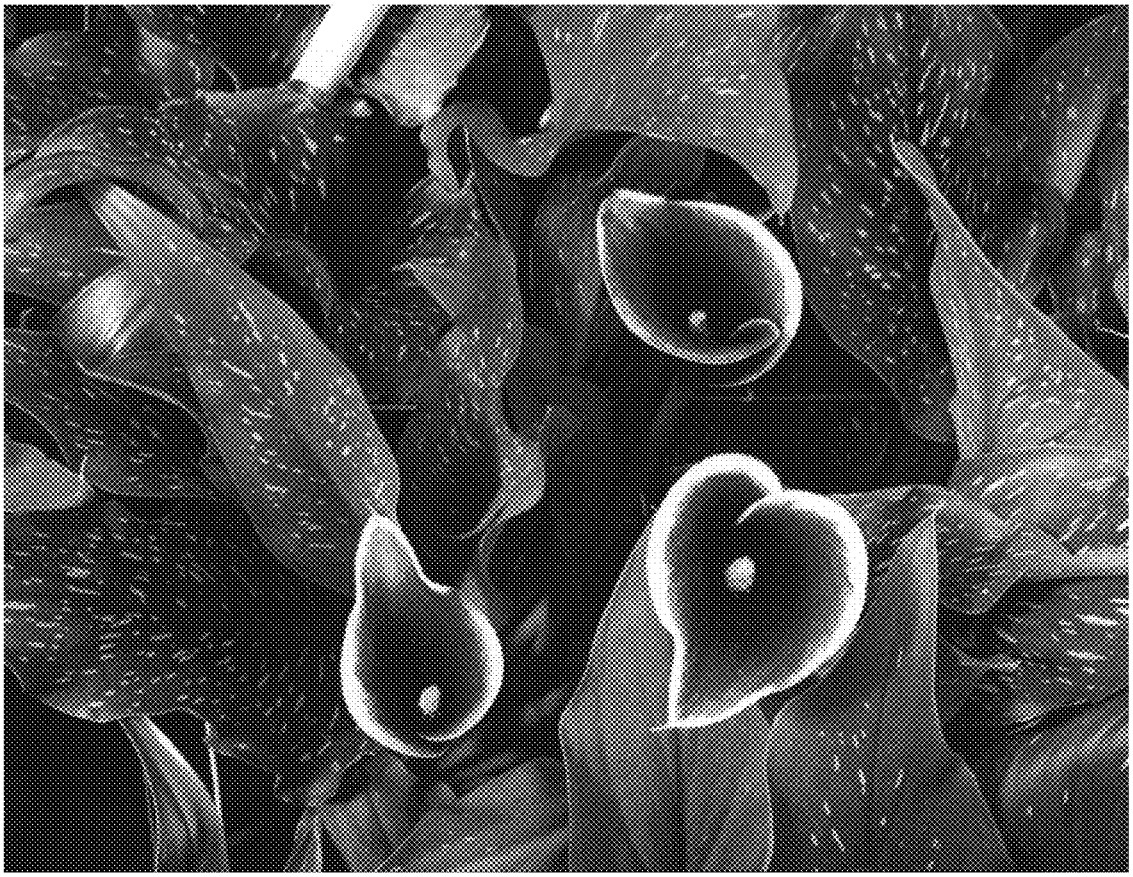

* * * * *